United States Patent [19]
Forster et al.

[11] Patent Number: 4,916,077
[45] Date of Patent: * Apr. 10, 1990

[54] METHOD AND APPARATUS FOR OXIDATIVE DECOMPOSITION AND ANALYSIS OF A SAMPLE

[75] Inventors: Alan R. Forster; Gregory J. Kamla, both of Houston, Tex.

[73] Assignee: Shell Oil Company, Houston, Tex.

[*] Notice: The portion of the term of this patent subsequent to Feb. 27, 2007 has been disclaimed.

[21] Appl. No.: 253,549

[22] Filed: Sep. 28, 1988

Related U.S. Application Data

[63] Continuation of Ser. No. 20,295, Feb. 27, 1987, abandoned.

[51] Int. Cl.⁴ ............................................. G01N 31/12
[52] U.S. Cl. ...................................... 436/160; 261/76; 261/78.2; 422/78; 422/80; 422/94; 436/177; 436/181
[58] Field of Search .................................. 436/116–118, 436/119, 122, 124, 155, 160, 181, 177; 422/78, 80, 94; 261/76, 78.2

[56] References Cited

U.S. PATENT DOCUMENTS

| | | | |
|---|---|---|---|
| 3,853,474 | 12/1974 | Austin | 422/94 X |
| 3,904,366 | 9/1975 | Grasenick | |
| 3,904,368 | 9/1975 | Takeyama et al. | 422/94 X |
| 3,923,464 | 12/1975 | Sitek et al. | |
| 4,018,562 | 4/1977 | Parks et al. | |
| 4,160,802 | 7/1979 | White et al. | 422/68 |
| 4,161,281 | 7/1979 | Erb et al. | |
| 4,161,282 | 7/1979 | Erb et al. | |
| 4,205,550 | 6/1980 | Swanson | |
| 4,228,795 | 10/1980 | Babington | |
| 4,261,511 | 4/1981 | Erb et al. | |
| 4,282,183 | 8/1981 | Bredeweg et al. | 422/78 |
| 4,351,801 | 9/1982 | Bartke | 422/78 |
| 4,352,779 | 10/1982 | Parks | 422/52 |
| 4,352,781 | 10/1982 | O'Brien | 422/78 |
| 4,367,042 | 1/1983 | Smith, Jr. et al. | 356/315 |
| 4,569,918 | 2/1986 | Moore et al. | 422/80 |
| 4,582,654 | 4/1986 | Karnicky et al. | 261/91 |
| 4,620,670 | 11/1986 | Hughes | |

OTHER PUBLICATIONS

"Determination of Total Sulfur in Hydrocarbons by Oxidative Microcoulometry", Moore, R. T., Clinton, P. and Barger, V. Analytical Chemistry, vol. 52 (1980) pp. 760-765.

"Determination of Low Level of Sulfur in Organics by Combustion Microcoulometry" White, D. C. Analytical Chemistry, vol. 49, No. 11 (1977) pp. 1615-1618.

"Probeneintragssytem mit Probenverbrennung oder Probenvorverdampfung fur die direkte Festsoffanalyse und fur die Losungsspektralanalyse," Berndt, H., Spectrochimica Acta. vol. 39B, Nos. 9-11 (1984) pp. 1121-1128.

"Venturi Jet (Atomizer)-Type Burner for Determining Sulfur in Light Petroleum Products", Brown, C. W., Analytical Chemistry, vol. 32, No. 3 (1960) pp. 442-443.

"Advances in Wickbold Combustion Technique", Kunkel, E., Mikrochimca Acta. [Wein] (1976) II, pp. 1-8.

"Determination of Nitrogen in Petroleum Fractions by Combustion with Chemiluminescent & Detection of Nitric Oxide", Drushel, H. V., Analytical Chemistry, vol. 49, No. 7 (1977) pp. 932-934.

"Direct Liquid Sample Introduction for Flow Injection Analysis and Liquid Chromatography with Inductively Copuled Argon Plasma Spectrometric Detection", Lawrence K. E. (Rice, G. W., and Fassel, J. A., Analytical Chemistry, vol. 56, (1984) pp. 289-292.

"On the Determination of Oxygen in Organic Solvents Using Inductively Coupled Plasma", Hauser, P. C. and Blades, M. N. Applied Spectroscopy, vol. 39, No. 5 (1985) pp. 872-877.

*Primary Examiner*—Barry S. Richman
*Assistant Examiner*—Jill Johnston

[57] ABSTRACT

Methods and apparatus are provided for decomposing and analyzing a sample. The methods combust a nebulized sample in an oxygen-rich atomsphere; the analysis method then analyzes the combustion gases for a preselected analyte. The apparatus employs a nebulizer operatively connected to a combustion tube; the analysis apparatus employs appropriate detector(s) to analyze the combustion gases from the combustion tube for preselected analyte(s).

8 Claims, 3 Drawing Sheets

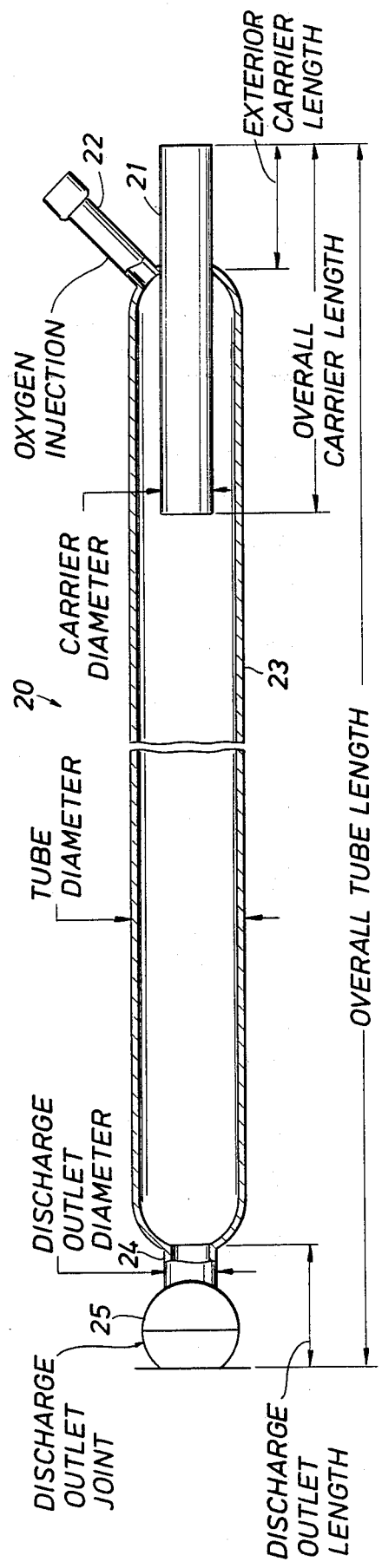
FIG. 2
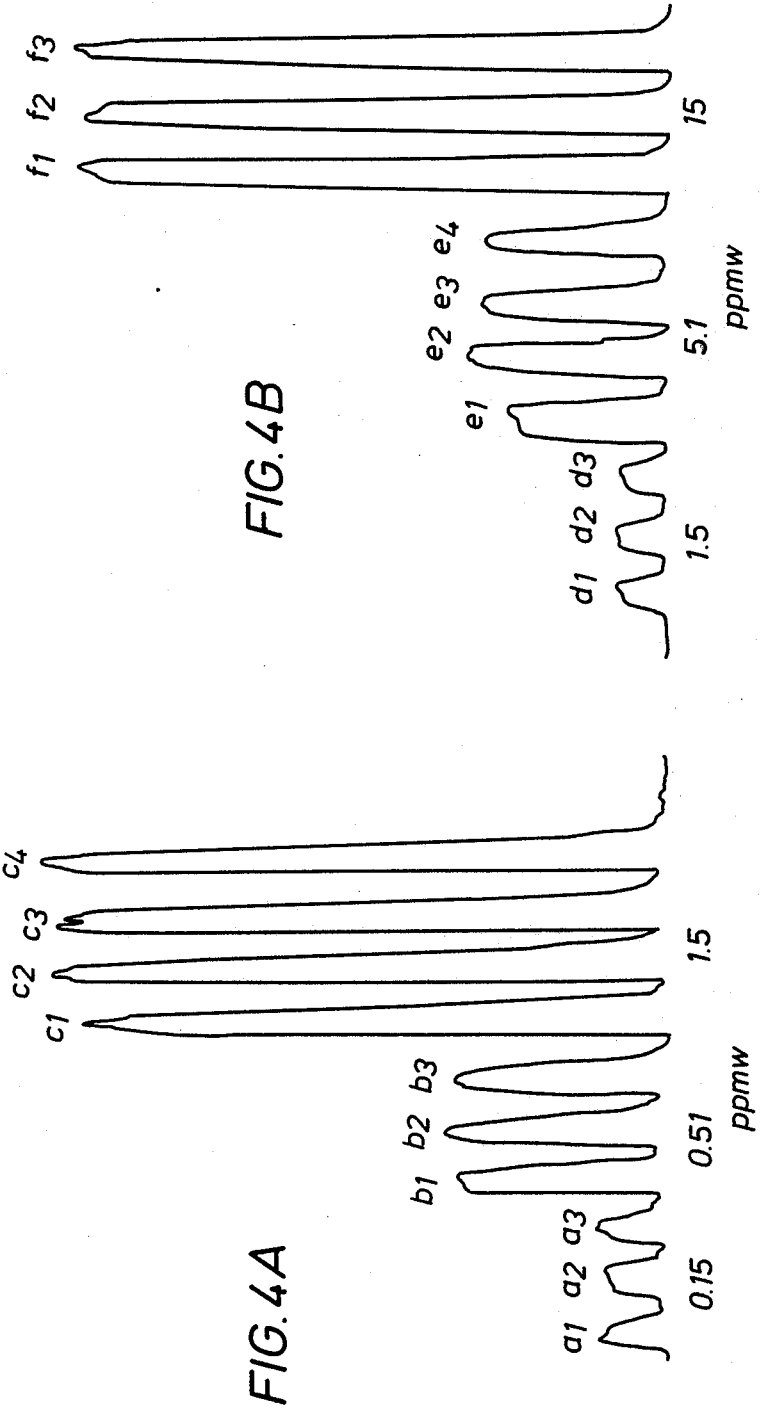
FIG. 4A
FIG. 4B

METHOD AND APPARATUS FOR OXIDATIVE DECOMPOSITION AND ANALYSIS OF A SAMPLE

This is a continuation of application Ser. No. 020,295, filed Feb. 27, 1987, now abandoned.

CROSS-REFERENCE TO SIMULTANEOUSLY FILED RELATED APPLICATIONS

"Method and Apparatus for Reductive Decomposition and Analysis of a Sample", A. R. Forster and G. J. Kamla, Ser. No. 07/253,550.

"Method and Apparatus for Analysis of a Sample for Nitrogen", A. R. Forster and G. J. Kamla, Ser. No. 07/249,256.

"Method and Apparatus for Analysis of a Sample for Sulfur", A. R. Forster and G. J. Kamla, Ser. No. 07/245,255.

BACKGROUND OF THE INVENTION

This invention relates to analysis of materials, and more particularly, relates to method and apparatus for the oxidative decomposition and quantitative determination of constituents of a sample.

A common form of sample preparation for elemental analysis involves the combustion of a sample followed by the use of the combustion gases from this sample for the detection of the desired constituent(s) or analyte(s). Examples of this include halogen and sulfur determination using microcouloumetry, nitrogen determination by chemiluminescence of excited state nitrogen dioxide, sulfur determination using $SO_2$ fluorescence, and carbon and hydrogen determination by gravimetric or Pregl-Dumas techniques. With the exception of carbon and hydrogen determinations, there is a problem associated with the combustion process which can cause unreliable analytical results and this problem centers on the sample introduction step.

If the sample is introduced using a styringe needle the needle must be placed directly into or very close to the hot zone of a combustion furnace to ensure the sample is transferred into the combustion zone and combusted therein. Unfortunately, heavy organic fractions or salts can remain within the needle and possibly clog it temporarily, or permanently, as well as the hostile environment damaging the needle. One approach taken to overcome this problem is to introduce the sample into the hot portion of the furnace using a small boat which has been loaded with the sample when the boat was positioned in a relatively cool portion of the furnace tube. In either case, however, the sample introduction and subsequent combustion is a transient process. Therefore, the oxygen concentration in the combustion tube changes over time during this process. This can be detrimental in cases where equilibria involving oxygen are important to the instrumental stability, sensitivity, or detection limits.

Accordingly, there is a need for a sample introduction scheme to allow for longer integration times in the detection phase which would then improve detection limits and also allow for use as an on-line monitor in process control, or as a chromatographic detector.

These and other limitations and disadvantages of the prior art are overcome by the present invention, however, and improved methods and apparatus are provided for decomposition and analysis of samples.

SUMMARY OF THE INVENTION

In a preferred embodiment of the present invention, methods and apparatus are provided for the quantitative determination of preselected constituents of a sample. In the presently preferred method for the analysis of a sample, the sample is first prepared for analysis by mixing a preselected quantity of the sample with a preselected quantity of a preselected material; the preselected material may serve to dilute and dissolve the sample, although the sample itself may also serve as this material. When the sample is the material, the analysis may be conducted substantially continuously. This sample and/or material (hereinafter sometimes referred to as "sample/material") may then be nebulized; the sample/material is nebulized in a nebulizer zone where an inert gas, such as argon, is used to disperse the sample/material into fine droplets which form an aerosol with the argon gas. The aerosol is then transported to an oxygen-rich combustion zone where the nebulized sample is completely burned and decomposed. The decomposed combustion products of the sample are then transported to an appropriate detection zone. In the detection zone the decomposed constituents of the sample are analyzed for preselected constituent(s) or analyte(s). Other methods, employing the initial portions of the above steps, may also be used to decompose a sample.

The presently preferred apparatus of the present invention is a nebulizer device positioned to deliver a liquid sample/material into the hot region of a combustion tube. A continuous aerosol stream of an appropriate preselected material and/or sample is injected into the combustion tube through the nebulizer with an argon carrier gas; the carrier gas serves to convert the preselected material and/or sample in the nebulizer into an aerosol form which becomes fully vaporized before it enters the combustion region of the combustion tube, where it is completely combusted. A small portion of sample may be substantially continuously injected, with or without the preselected material, into the nebulizer by an appropriate pump, thereby providing for a substantially continuous portion of the sample to be combusted in the combustion tube. The sample may be dissolved and/or diluted in the material, or for appropriate samples only the sample may be injected into the combustion tube, via the nebulizer. The combustion tube is supplied with oxygen to ensure complete combustion of the preselected material and/or the sample. The combustion products from the combustion tube are exhausted through an appropriate discharge opening and may then be dried and/or filtered prior to passage to an appropriate detector, such as, for example, but not limited to an $SO_2$ or NO analyzer. The output of the detectors may in turn be connected to an appropriate recorder or controller. Other apparatus, similar to that noted above (less the detectors), may be employed to decompose a sample.

It is an object of the present invention to provide apparatus and methods for decomposing a sample.

It is an object of the present invention to provide an apparatus for quantitative analysis of preselected constituents of a sample.

It is also an object of the present invention to provide a method for quantitative analysis of preselected constituents of a sample.

It is a specific object of the present invention to provide a method for analyzing a sample, comprising, nebulizing said sample, transporting said nebulized sample to a decomposition zone, decomposing said sample in an oxygen-rich atmosphere of oxygen and an inert gas at a temperature sufficient to ensure complete combustion of said sample, transporting said decomposed sample to a detection zone, and analyzing said decomposed sample for a preselected analyte.

These and other advantages and objects of the present invention will become apparent from the following detailed description wherein reference is made to the Figures in the accompanying drawings.

IN THE DRAWINGS

FIG. 2 is a simplified cross-sectional diagram depicting the arrangement of a combustion tube for use in the apparatus of the present invention.

FIG. 4 is a simplified representation of the data collected by the preferred embodiment of the present invention illustrating the presence of a preselected constituent of a sample.

DETAILED DESCRIPTION OF THE INVENTION

Figure 1:
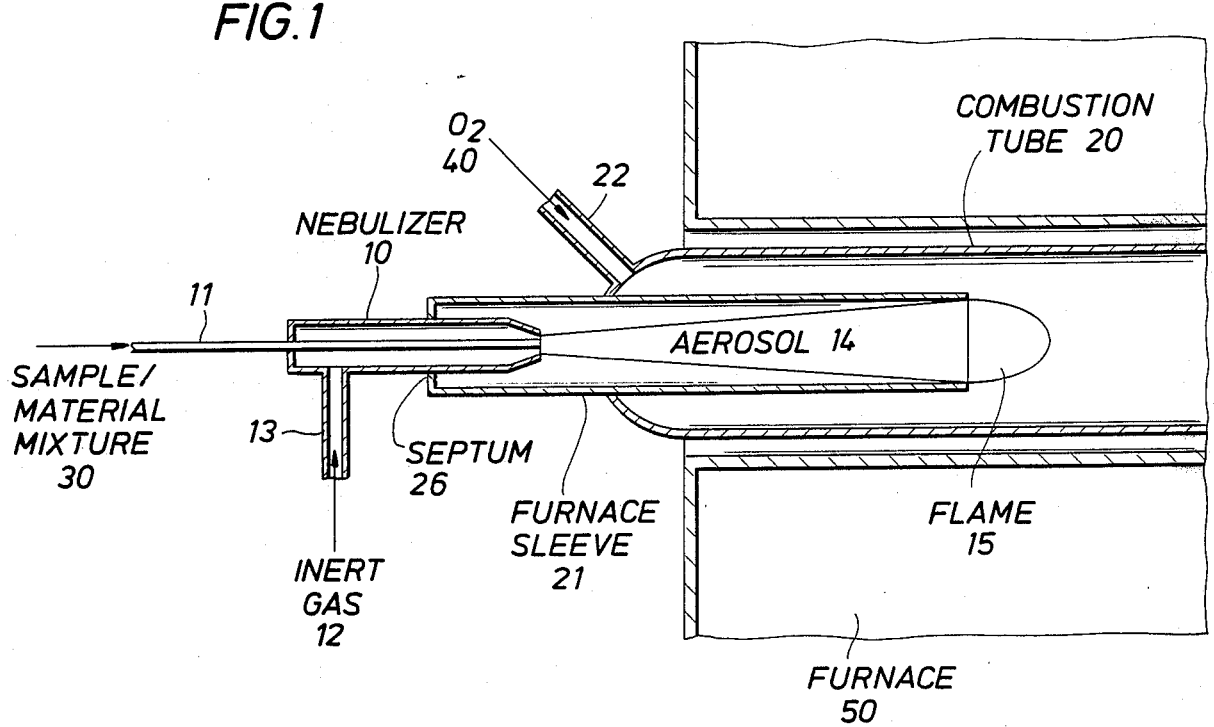
FIG. 1 is a simplified functional diagram depicting the general arrangement of a nebulizer and combustion tube for use in the apparatus or methods of the present invention.

The present invention provides methods and apparatus for quantitative determinations of preselected constituents (analytes) of a sample, and for decomposition of a sample. Referring now to FIG. 1, there may be seen a simplified functional diagram depicting the general arrangement of a nebulizer 10 and combustion tube 20 for use in the apparatus or methods of the present invention. More specifically, it may be seen that the present invention employs a nebulizer 10 operatively connected to a combustion tube 20. In particular, it may be seen that the sample and/or material 30 is injected into the nebulizer 10 via inlet 11 with or without a stream of preselected material, which may be a liquid solvent stream. A stream of inert gas 12, such as for example, but not limited to argon, is also supplied to the nebulizer 10 via inlet 13 to turn the sample and/or material stream 30 into an aerosol 14 which then is transported by the argon 12 into the combustion tube 20. The combustion tube 20 is supplied with oxygen 40 via inlet 22 and may be externally heated by furnace 50 to maintain an appropriate hot zone for complete combustion. The sample and/or material 30 are vaporized in the furnace sleeve 21 (hereinafter "sample carrier sleeve" or "carrier tube") and the vapors exit this sleeve 21 to reach the proper combustion temperature. Upon reaching the hot zone, the material and/or sample 30 combust in the oxygen atmosphere. Under appropriate circumstances, as noted later herein, the sample may also be the preselected material.

Since the nebulizer 10 is positioned in a relatively cool region at the front end of the combustion tube 20, the chances of the sample transport system becoming damaged or clogged, as in the prior art are eliminated. Thus, a sample introduction scheme, which may be substantially continuous, may be easily maintained.

There are several important aspects of this invention which must be properly followed. Careful placement of the nebulizer 10 relative to the hot portion of the furnace tube 20 and the inlet 22 for oxygen gas is presently considered very important. It is necessary to position the nebulizer 10 relatively close to the hot zone so that the sample and/or material 30 does not contact a cool furnace tube 20 wall. The nebulizer 10 is held in place within the cool end of the combustion tube 20 using a septum 26 constructed of an appropriate material, such as, for example, but not limited to silicone.

The oxygen 40 is preferably added close to the beginning of the hot region, although, as noted later herein, the exact location is not critical. The oxygen supply 40 must be free of the constituents for which the sample is to be analyzed, or an appropriate adjustment to the data based upon the actual oxygen supply employed must be determined before or after a sample is analyzed. The argon 12 flow rate must be sufficient to effectively nebulize the sample and/or material and to transport the sample/material to the hot zone and yet remain low enough so that it does not dilute the vaporized gases to the point of inhibiting complete combustion of the sample. For high inert gas flow rates the inert gas may dilute the sample and may also limit the ultimate sensitivity of the instrumental detection schemes that may be employed to analyze the combustion products. The sample and/or material flow must be low enough so that complete combustion can occur without soot formation.

Merely increasing the gas flows to compensate for excess sample and/or material input may create excessive heat within the quartz furnace tube and may induce subsequent failure. Conversely, too little flow of sample and/or material makes it very difficult to support continuous combustion. A pump, preferably with a precision flow output, such as for example, but not limited to an HPLC pump, is necessary for material and/or sample delivery to the nebulizer 10. A typical sample flow rate (depending upon the material type) is approximately 100 micro liters per minute ($\mu$l/min). Sample introduction may be achieved using an HPLC injection valve and sample loop, with the pump pushing the sample in the sample injection loop (not shown) with an appropriate deaerated material from a material supply reservoir. (See FIG. 3) Alternatively, the sample may be the material, or the sample may be dissolved and/or diluted by the material by mixing a preselected quantity of sample in a preselected quantity of material to achieve a known sample concentration.

The supply of oxygen and argon into the combustion tube provides a positive pressure in the combustion tube, to exclude any undesirable gases. The discharge end of the combustion tube is also at a pressure slightly higher than atmospheric pressure (See FIG. 2). This allows the combusted sample products to be positively swept from the combustion tube into subsequent sample discharge tubing. Thus, this configuration of nebulizer 10 and combustion tube 20 provide methods and apparatus for sample decomposition. The sample discharge tubing may then be connected to appropriate detection apparatus after drying and filtering, if necessary.

The connection between the combustion tube and the detector may include a membrane dryer to remove any water produced during combustion and a filter of appropriate pore size (preferably about 5 $\mu$m pore size) to prevent contamination of the detector in the event of soot formation during combustion. (See FIG. 3) A tee-fitting with one leg open, may be used at the input of such a detector to ensure atmospheric pressure at the detector input, if the detector requires samples at atmospheric pressure. Thus, this configuration of equipment provide methods and apparatus for analyzing a sample for preselected constituents.

Referring now to FIG. 2 there may be seen a simplified depiction of the arrangement of a combustion tube 20 for use in the apparatus of the present invention. More particularly, the combustion tube 20 is seen to consist of an outer envelope 23 of preferably quartz with an inlet 22 for injecting oxygen into the tube and with an outlet neck 24 and joint 25 at the opposite end for removal of any combustion gases. This outlet joint 25 is preferably a glass to quartz connection joint.

Also shown is the furnace sample carrier sleeve 21 (or carrier tube) which allows for the introduction of a sample into the combustion tube 20. For the present invention an appropriate septum 26 and nebulizer 10 are inserted into the exterior opening of this sleeve 21 (as shown functionally in FIG. 1).

The length of the furnace tube is sized to allow for its use in an external furnace 50, such as for example, but not limited to a Dohrmann Model S-300 pyrolysis furnace; Dohrmann sells several commercial models of such furnaces. Once the length is thus roughly selected, the volume of the furnace tube is maximized to allow for larger sample and/or material injection rates while still achieving complete combustion of such materials and/or samples; this is generally accomplished by maximizing the outside diameter of the tube so that it narrowly fits inside the opening for a furnace tube in the external furnace 50.

The sample carrier sleeve 21 also has as large a diameter as possible to allow for a larger sample and/or material injection rates and has a length to ensure substantially complete vaporization of the sample/material before the sample/material exits the sleeve into the oxygen atmosphere of the furnace tube. A sleeve length of about twenty percent of the furnace tube length has been found to be satisfactory from experimental determination. A small amount of oxygen may also be introduced with the sample/material to avoid the formation of coke on this sleeve 21 during vaporization; this is most easily accomplished by injecting a small flow of oxygen into the nebulizer 10 via inlet 13 with the inert gas 12.

The combustion oxygen supply is preferably injected at the cool end of the tube, which is located physically outside the external furnace 50. This arrangement allows for a continuous, maximum outside diameter combustion tube of maximum volume to be contained in the external furnace 50. The exact point of injection of oxygen has been found to not be a critical aspect of the invention and may be located in the middle of the tube, or even at or near the discharge end of the tube. Preferably, however, this inlet 22 is adjacent the cool end as depicted.

The volume of the furnace tube 20 and the volume of the sample carrier sleeve 21 must be balanced versus the flow rates of oxygen 40 and sample/material/inert gas aerosol 14 to ensure substantially complete vaporization before leaving the sleeve 21 (without coking) and to ensure complete combustion (without soot formation) before leaving the furnace tube 20. However, the inert gas 12 flow rate is principally determined by the selection of the nebulizer 10, since the nebulizer 10 determines the minimum inert gas flow rate capable of efficiently nebulizing the sample/material. The combustion tube may optionally contain baffles, constrictive necks, and/or quartz chips to provide positive mixing of gases and vapors to ensure complete combustion.

For the Dohrmann Model S-300 pyrolysis furnace the quartz furnace tube has: an overall length of 575 mm, an outside diameter of 22 mm, a 6 mm outside diameter oxygen injection line, a 12 mm outside diameter discharge outlet, a discharge outlet length of 25 mm, a carrier tube outside diameter of 12 mm, an overall carrier tube length of 76 mm, and an exterior carrier length of 25 mm.

Figure 3:
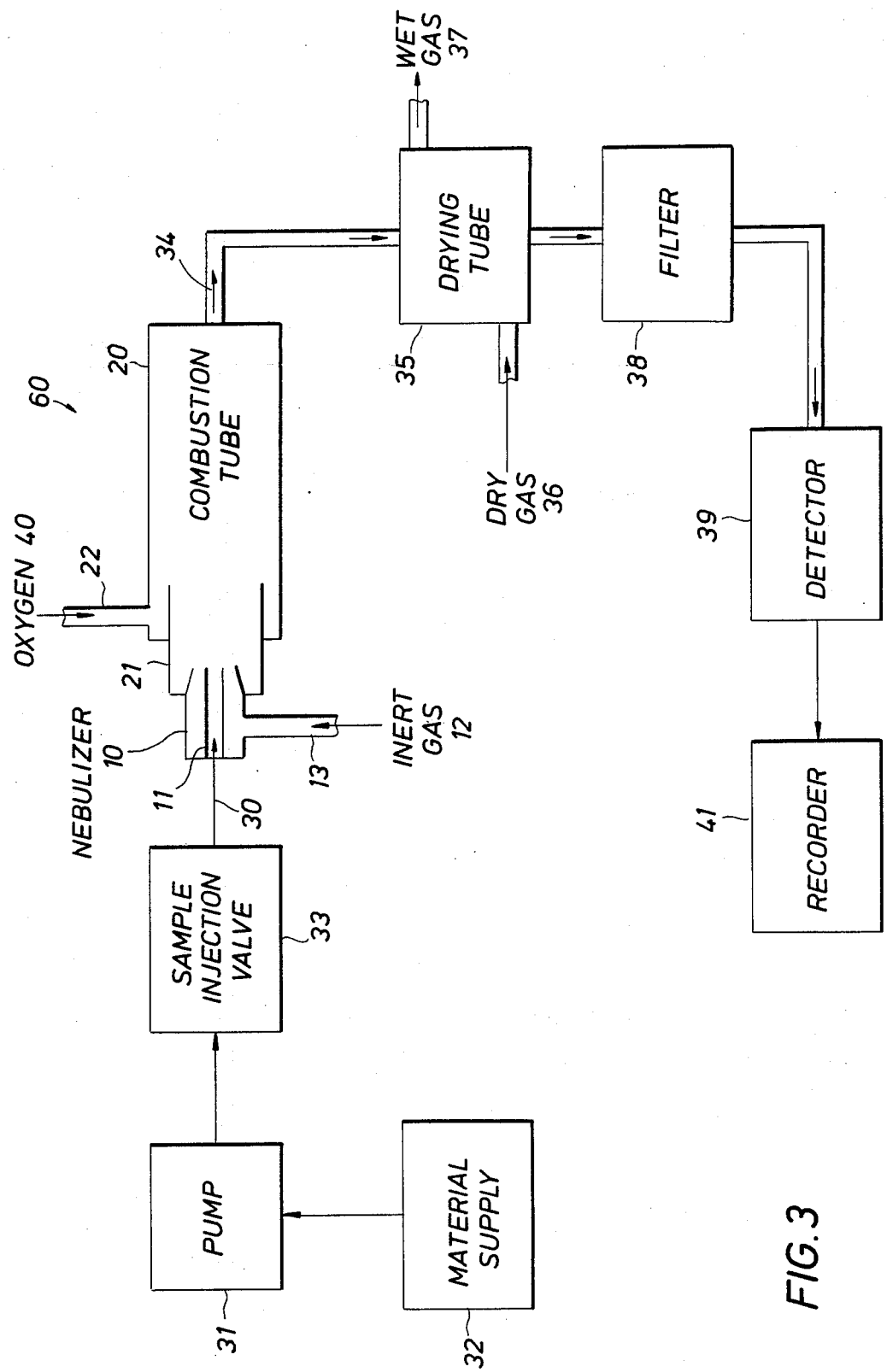
FIG. 3 is a simplified functional diagram of one embodiment of the apparatus of the present invention.

Referring now to FIG. 3, there may be seen a simplified functional diagram of one embodiment of the apparatus 60 of the present invention. More particularly, there may be seen a depiction of the nebulizer 10 and combustion tube 20, as previously shown and described for FIG. 1, as well as other items. There may be seen pump 31 (as described hereinbefore), interconnected with material supply 32, for delivering at a controlled rate, material to sample injection valve 33. The sample injection valve 33 may be operated to inject a fixed portion of the sample 30 (depending upon the length of the sample loop—not shown), at a controlled rate, into the nebulizer 10. For each such separate injection of sample, the sample stream replaces the material stream; accordingly, the sample must be introduced over a long enough time to ensure steady-state combusion, or the differences in chemical and combustion characteristics between the sample and material must be minimized, so that the sample portion from the sample loop does not significantly perturb the flame 15 (see FIG. 1). Alternatively, the sample may be dissolved and/or diluted in the material and this mixture of sample and material injected, at a controlled rate, by pump 31 into the nebulizer 10.

The nebulizer 10, as described hereinbefore, nebulizes the sample/material 30 stream which is then completely combusted in the combustion tube 20. The tube's discharge gases 34 are preferably dried by drying tube 35 to remove any water vapor and filtered by filter 38 to remove any soot before passing the combustion gases into an appropriate detector 39. The detector 39 analyzes these gases for a preselected constituent or analyte. Although only one detector 39 is depicted, more than one detector may be so employed. The detector 39 output may be recorded on an appropriate recorder 41 or used as an input to an appropriate controller (not shown). When more than one detector 39 is employed, the flow rates may need to be increased to provide enough combustion gases for the number of detectors employed.

The sample/material 30 may be totally sample, if the sample is a liquid at room temperature and capable of being nebulized. Any preselected material employed must dissolve the sample (solid or liquid), combust with no soot (if enough oxygen is present), be liquid at room temperature and be extremely pure, i.e. an HPLC grade solvent. Examples of such materials are iso-octane, toluene, and decalin. For aromatic samples/materials, the injection rates must usually be lowered to prevent sooting of the furnace tube. A sample/material flow rate of about 100 $\mu$l/min has been found to be satisfactory for the hardware configuration described later herein with respect to FIGS. 3 and 4. Typically, the sample/material flow rate is about 100 $\mu$l/min for iso-octane and about 30 $\mu$l/min for toluene, since toluene is more aromatic than iso-octane. The sample/material flow rate may be controlled by an appropriate liquid flow control device (not shown).

The minimum inert gas 12 flow rate is chiefly determined by the size of the nebulizer 10; this flow rate must be sufficient to ensure the nebulizer nebulizes the sample/material 30 in an efficient and continuous manner. Higher inert gas rates tend to dilute the sample but may be acceptable from a detection limit point of view. The inert gas flow rate may be controlled by an appropriate gas flow control device (not shown).

The oxygen 40 flow rate into the furnace tube 20 is, as a minimum, high enough to ensure complete combustion; although at very high rates, excessive sample dilution may occur and certain detectors may be quenched. However, the flow rate must also be high enough to prevent sooting. In addition, a small amount of oxygen is preferably injected into the nebulizer along with the inert gas to prevent the sample/material from coking up the sleeve 21; this oxygen flow rate should be about 5 to 10 percent of the inert gas flow rate going into the nebulizer. Further, as noted hereinbefore, the oxygen supply 40 is preferably free of the constituents for which the sample is to be analyzed. The oxygen flow rate may be controlled by an appropriate gas flow control device (not shown).

As indicated hereinbefore the volume and length of the furnace tube is chiefly determined by the external furnace 50 to be employed. Once the furnace tube 20 size is determined the carrier tube 21 size is then determined. Again, a maximum diameter is desired to maximize the possible range of sample injection rates. The length of the carrier tube 21 is about 20 percent of the furnace tube 20 length, although shorter and longer lengths have been found to work satisfactorily. If the carrier tube 21 length is too short, the combustion will flicker and be sporatic due to incomplete vaporization. If the carrier tube 21 length is too long, the walls of the carrier tube 21 may eventually become coated with sample/mixture films. The carrier tube 21 also keeps the sample 30 from the oxygen 40 to prevent flash-backs to the nebulizer 10. Although the carrier tube 21 serves to protect the nebulizer 10 to provide for long-term sample injection stability, it may be completely removed and still be within the scope of the present invention.

The nebulizer 10 size is in turn chiefly determined by the physical dimensions of the carrier tube 21, and accordingly the furnace tube 20. That is, the nebulizer 10 must be physically small enough to at least partially fit inside the inner diameter of the carrier tube 21 (as depicted in FIG. 1).

As also noted hereinbefore, the flow rate of inert gas 12 into the nebulizer 10 is chiefly determined by the size and type of nebulizer 10. The minimum flow rate is that which still effectively nebulizes the sample/mixture and the maximum flow rate is determined by the sample residence time in the hot zone; at too high a flow rate the sample passes through the hot zone before combustion occurs or is completed. As noted hereinbefore, any oxygen injected into the nebulizer is at a rate about 5–10 percent of the inert gas injection rate.

As previously noted herein, the oxygen flow rate must be sufficient to completely combust the sample. Thus, the minimum oxygen flow rate is determined by the sample injection rate, which is in turn related to the nebulizer size and type, and the inert gas flow rate. The oxygen flow rate is at least equal to, but preferably greater than, the inert gas flow rate; as long as this flow rate is still a sufficient flow rate to provide enough oxygen to completely combust the sample.

The sample flow rate is thus chiefly determined by the nebulizer size and type, and the inert gas flow rate, i.e. these rates/sizes must be sufficient to efficiently nebulize the sample.

In general, the volume of the furnace tube (in liters) divided by the sum of the inert gas and oxygen flow rates (in liters/min) may be in the range from 0.05 to 1 or larger. The low (0.05) end of the range is for oversized nebulizers on small volume furnace tubes and the high (1) end of the range is for small nebulizers and large furnace tubes. However, the high end of the range may result in decreased sensitivity of detection for particular analytes.

A specific example of items for the detection of sulfur is as follows:

Thermo Electron Instruments Model 43A pulsed Fluorescence $SO_2$ analyzer (Thermo Electron Instruments is now named Thermo Environmental Instruments)

Beckman 100A HPLC pump, with an appropriate pulse dampener

Dohrmann Model S-300 pyrolysis furnace

VERIFLO flow controllers as flow control devices
two—Model SC423BXFT
one—Model SC423BFT J. E. Meinhard Assoc. nebulizer Model TR-30-A1

Quartz pyrolysis furnace tube with glass elbow adapter and with silicone septa

Perma-Pure Dryer Model PD-6-12p membrane dryer

Cole-Parmer Company Model TV-6623-20 In-Line TFE

Filter holder and model TV-6623-51 47 mm diam TFE filters Various valves, piping, tubing, columns and connectors.

Referring now to FIG. 4, there may be seen the results from the hereinbefore described items connected together, as noted in FIG. 3, to detect sulfur. These results are for different concentrations of n-dibutyl sulfide dissolved in iso-octane. The Thermo Electron Instruments Model 43A has several ranges and was run on a low (0.1 ppm) range and a high (1.0 ppm) range, as depicted in FIGS. 4A and 4B, respectively. Multiple samples of standard solutions with the noted sulfur concentrations were run as follows: $a_i$ (0.15 ppmw), i=1 to 3; $b_i$ (0.51 ppmw), i=1 to 3; $c_i$ (1.5 ppmw), i=1 to 4; $d_i$ (1.5 ppmw), i=1 to 3; $e_i$ (5.1 ppmw), i=1 to 4; and $f_i$ (15 ppmw) i=1 to 3. These multiple samples demonstrate the reproducibility of the apparatus and methods of the present invention. For these data the following flow rates were employed: argon—300 ml/min; sample/material—100 μl/min; oxygen—430 ml/min; and oxygen into the nebulizer—30 ml/min. However, the flow rates for this combination of equipment may be scaled up or down and still have approximately the same analyte (sulfur) sensitivity over the following ranges: argon—0.1 to 1-2 l/min; sample/material—0.01 to 0.5 ml/min; and oxygen—0.2 to 2 l/min. Use of such an apparatus has resulted in a limit of detection for sulfur which has an approximate threshold of about 20 parts per billion weight (ppbw).

Figure 5:
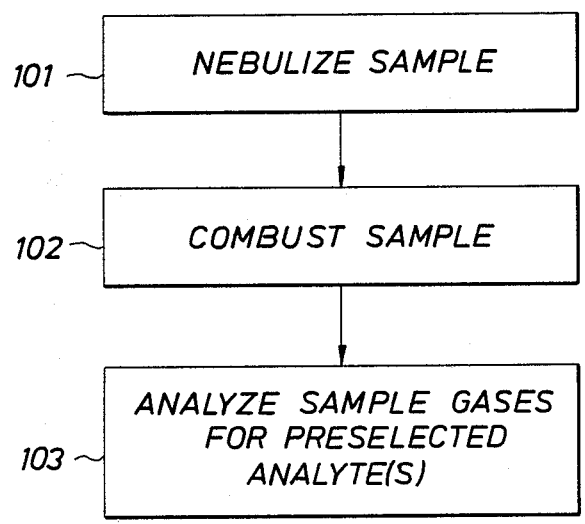
FIG. 5 is a simplified flow chart of the basic steps of the preferred method of the present invention.

Thus, it may be seen that the present invention provides methods for decomposing and/or analyzing a sample for preselected analyte(s). FIG. 5 depicts the basic steps of the methods of the present invention. In particular, the analysis method of the present invention nebulizes the sample/material 101, combusts this nebulized sample 102, and then analyzes the gases from the combusted sample for preselected analytes 103. However, the decomposition method nebulizes the sample/material 101 and then combusts this nebulized sample 102; thus, the decomposition method only employs the first two basic steps (blocks 101 and 102) depicted in FIG. 5.

When samples containing nitrogen compounds are combusted, the nitrogen is converted to nitrogen oxides (NO or $NO_2$). Any nitrogen oxides in the combustion gases may be detected using a chemiluminescence detector, a laser-excited fluorescence detector, and/or a mass spectrometer. Preferably nitrogen is detected through the use of chemiluminescence. There are two types of chemiluminescence detectors. The presently preferred type involves the gas-phase chemiluminescent reaction of ozone with nitric oxide (NO). The other type is a gas/liquid-phase chemiluminescent reaction of nitrogen dioxide and luminol.

When samples containing sulfur compounds are combusted, the sulfur is converted to sulfur dioxide and sulfur trioxide ($SO_2$ and $SO_3$). The oxides of sulfur may be detected using fluorescence, microcoulometry, and/or mass spectrometry. Preferably sulfur would be detected by ultraviolet excitation of $SO_2$ with subsequent fluorescence detection at a visible wavelength. Microcoulometric titrations of $SO_2$ with iodine may be performed by sampling the combustion gases in a titration cell.

When samples containing halogen compounds (fluorine, chlorine, bromine, and/or iodine) are combusted, the halogens are converted to their halide and oxyhalide forms. These species may be detected in the combustion gases by microcoulometry, conductivity, gravimetry, and/or mass spectrometry. The preferred method is microcoulometry which employs a silver/halide titration (applicable for all halides with the exception of fluoride).

When samples containing carbon compounds undergo complete combustion, the carbon is converted to carbon dioxide. The carbon dioxide in the combustion gases may be detected using an infra-red detector, gravimetry, Pregl-Dumas technique, and/or mass spectrometry. The infra-red detector measures the infra-red absorbance of the combustion gases relative to a standard reference cell of carbon dioxide gas in a mixture of gases similar to the combustion gases. In the Pregl-Dumas method, the thermal conductivity of the combustion gases is measured before and after absorption of the carbon dioxide.

When samples containing hydrogen are combusted, the hydrogen is converted to water. The water in the combustion gases may be detected using gravimetry, Karl Fischer titration, Pregl-Dumas, and/or mass spectrometric techniques. Karl Fischer titration for water employs a typical stabilized Karl Fischer reagent consists of iodine and sulfur dioxide in pyridine and methyl cellusolve. The reaction between water and the components within the Karl Fischer reagent reduces the iodine and this reduction of iodine is measured amperometrically.

In microcoulometry, a titration cell is maintained at a constant concentration of titrant ion through coulometric generation. Addition of the analyte species of interest depletes the concentration of the titrant ion. The current necessary to coulometrically maintain the titrant ion concentration is a measure of the amount of analyte species present. In mass spectrometry, the combustion gases are ionized, the ions are separated as a function of mass, and the ions of a predetermined mass or mass range are then detected. In gravimetry, the analyte of interest is chemically complexed to a substrate and the change in weight of the substrate is directly proportional to the analyte present. However, some consideration must be made, for the analytes sought to be detected and the types of samples to be analyzed, to prevent analyte interferences in a given detection technique that is capable of detecting more than one analyte sought to be detected.

For both sulfur and nitrogen detection, the methods and apparatus of the present invention lend themselves well to automated nitrogen or sulfur analysis in process contrl, or blending applications.

Many other variations and modifications may be made in theapparatus and techniques hereinbefore described, by those having experience in this technology without departing from the concepts of the present invention. Accordingly, it should be clearly understood that the apparatus and methods depicted in the accompanying drawings and referred to in the foregoing description, are illustrative only and are not intended as limitations on the scope of the invention.

What is claimed is:

1. A method for analyzing a sample, comprising:
    nebulizing in a cool zone at least a portion of said sample using an inert gas,
    transporting said nebulized sample to a decomposition zone located in a hot zone,
    decomposing said sample in an oxygen-rich atmosphere at a temperature sufficient to ensure complete combustion of said sample,
    transporting said decomposed sample to a detection zone, and
    analyzing said decomposed sample for a preselected analyte.

2. A method as described in claim 1, wherein said nebulizing step comprises,
    injecting a portion of said sample at a preselected rate into a nebulizing zone, and
    injecting an inert gas into said nebulizing zone at a preselected rate to form an aerosol with said injected sample.

3. Apparatus for analyzing a sample, comprising:
    means located in a cool zone for nebulizing at least a portion of such a sample to form an aerosol containing said portion of such a sample,
    means for decomposing said aerosol in an oxygen-rich atmosphere of oxygen and an inert gas at a temperature sufficient to ensure complete combustion of said portion of such a sample in said aerosol in said decomposition zone,
    means for transporting said portion of such a sample from said means for decomposing to a detection zone, and
    means for analyzing said portion of such a sample for a preselected analyte in said detection zone.

4. An apparatus as described in claim 3, wherein said means for nebulizing comprises,
    means for injecting a portion of such a sample at a preselected rate into a nebulizing zone, and
    means for injecting an inert gas into said nebulizing zone at a preselected rate to form an aerosol with said injection portion of such a sample.

5. Apparatus for analyzing a sample, comprising:
    a combustion tube with an inlet end containing therein a sample carrier tube, having an oxygen inlet adjacent said inlet end for supplying excess oxygen to said tube, and having at the opposite end from said inlet end a discharge end containing therein a combustion gases discharge outlet,
a nebulizer sealingly connected to said sample carrier tube so as to discharge into said carrier tube an aerosol of said sample and an inert gas, and
a detector connected to said outlet for analyzing combustion gases from said combustion tube for a preselected analyte.

6. An apparatus as described in claim 5, further comprising:
a pump connected to said nebulizer for supplying a portion of said sample to said nebulizer,
a dryer for drying combustion gases from said combustion tube connected to said outlet, and
a filter for filtering combustion gases from said combustion tube interconnected between said dryer and said detector.

7. Apparatus for decomposing a sample, comprising:
a combustion tube having an inlet end containing therein a sample carrier tube, having an oxygen inlet adjacent said inlet end for supplying excess oxygen to said tube, and having at the opposite end from said inlet end a discharge end containing therein a combustion gases discharge outlet, and
a nebulizer sealingly connected to said sample carrier tube so as to discharge into said carrier tube an aerosol of said sample and an inert gas.

8. A method for decomposing a sample, comprising:
injecting a portion of said sample at a preselected rate into a nebulizing zone,
injecting an inert gas into said nebulizing zone at a preselected rate to form an aerosol with said injected sample,
transporting said nebulized sample to a decomposition zone, and
decomposing said sample in an oxygen-rich atmosphere of oxygen and an inert gas at a temperature sufficient to ensure complete combustion of said sample.

* * * * *